US012788327B2

(12) United States Patent
Dajles et al.

(10) Patent No.: US 12,788,327 B2
(45) Date of Patent: Nov. 10, 2026

(54) METHODS AND SYSTEMS FOR SENSING PARAMETERS IN IMPLANTABLE DEVICES

(71) Applicant: Establishment Labs S.A., La Garita (CR)

(72) Inventors: Denise Dajles, La Garita (CR); Juan José Delgado, La Garita (CR); Nathalia Araujo, La Garita (CR); Roberto De Mezerville, La Garita (CR); Juan José Chacón Quirós, La Garita (CR)

(73) Assignee: Establishment Labs S.A., La Garita (CR)

( * ) Notice: Subject to any disclaimer, the term of this patent is extended or adjusted under 35 U.S.C. 154(b) by 1000 days.

(21) Appl. No.: 17/765,962

(22) PCT Filed: Oct. 2, 2020

(86) PCT No.: PCT/IB2020/059287
§ 371 (c)(1),
(2) Date: Apr. 1, 2022

(87) PCT Pub. No.: WO2021/064686
PCT Pub. Date: Apr. 8, 2021

(65) Prior Publication Data

US 2022/0338808 A1 Oct. 27, 2022

Related U.S. Application Data

(60) Provisional application No. 62/909,318, filed on Oct. 2, 2019.

(51) Int. Cl.

*A61B 5/00* (2006.01)
*A61B 5/01* (2006.01)
(Continued)

(52) U.S. Cl.
CPC ............ *A61B 5/686* (2013.01); *A61B 5/0008* (2013.01); *A61B 5/0022* (2013.01);
(Continued)

(58) Field of Classification Search
CPC ..... A61B 5/686; A61B 5/0008; A61B 5/0022; A61B 5/0031; A61B 5/01; A61B 5/4851;
(Continued)

(56) References Cited

U.S. PATENT DOCUMENTS

| | | | |
|---|---|---|---|
| 9,673,516 | B2 | 6/2017 | Mejia |
| 10,176,412 | B2 | 1/2019 | Geissler et al. |

(Continued)

FOREIGN PATENT DOCUMENTS

| | | |
|---|---|---|
| BR | 112022006287 | 6/2022 |
| CA | 3156319 | 4/2021 |

(Continued)

OTHER PUBLICATIONS

Goodale, B. M. et al., "Wearable Sensors Reveal Menses-Driven Changes in Physiology and Enable Prediction of Fertile Window: Observational Study," *J. Med. Internet Res*, vol. 21, No. 4, pp. 1-14 (2019).

(Continued)

*Primary Examiner* — Jason M Sims
*Assistant Examiner* — Matthew Eric Ogles
(74) *Attorney, Agent, or Firm* — SCHWEGMAN LUNDBERG & WOESSNER, P.A.

(57) ABSTRACT

Medical implants including sensors are described. The implant may have a flexible shell with a base, wherein the plurality of sensors may be incorporated onto and/or into the shell. The plurality of sensors may be distributed at different locations of the shell. Each sensor of the plurality of sensors may be configured to measure one or more parameters such as, e.g., temperature and/or pressure, and may comprise an
(Continued)

electromagnetic coil useful for wireless transmission of data. Each sensor may be configured to transmit data at a frequency different from the frequency of one or more of the other sensors, may be configured to transmit data at a time different from a time data is transmitted by one or more of the other sensors, and/or may include a device identifier different from the device identifier of one or more of the other sensors.

20 Claims, 6 Drawing Sheets

(51) Int. Cl.
*A61B 10/00* (2006.01)
*A61B 90/00* (2016.01)
*A61F 2/12* (2006.01)

(52) U.S. Cl.
CPC .............. *A61B 5/0031* (2013.01); *A61B 5/01* (2013.01); *A61F 2/12* (2013.01); *A61B 5/4851* (2013.01); *A61B 2010/0019* (2013.01); *A61B 2090/3966* (2016.02); *A61B 2562/046* (2013.01)

(58) Field of Classification Search
CPC .... A61B 2010/0019; A61B 2090/3966; A61B 2562/046; A61B 5/4312; A61B 5/4343; A61B 10/0012; A61B 2562/0247; A61B 2562/0271; A61B 2562/08; A61B 2562/12; A61B 2562/162; A61B 5/015; A61B 5/064; A61B 5/6861; A61B 5/7495; A61F 2/12; A61F 2/0059; A61F 2/02; A61F 2250/0002; A61F 2250/0085; A61F 2250/0098; A61M 2205/04; A61M 2205/3327; A61M 2205/3344; A61M 2205/3368; A61M 2205/3523; A61M 2205/3569; A61M 2205/505; A61M 39/02
See application file for complete search history.

(56) References Cited

U.S. PATENT DOCUMENTS

| | | | | |
|---|---|---|---|---|
| 10,424,837 | B2 | 9/2019 | Mejia | |
| 10,824,925 | B2 | 11/2020 | Geissler et al. | |
| 2007/0027367 | A1* | 2/2007 | Oliver | A61B 5/0024 128/903 |
| 2009/0275815 | A1 | 11/2009 | Bickoff et al. | |
| 2011/0152913 | A1* | 6/2011 | Jones | A61B 34/25 623/8 |
| 2011/0208302 | A1* | 8/2011 | Glicksman | A61F 2/12 623/8 |
| 2012/0302874 | A1 | 11/2012 | Hollstien | |
| 2013/0338769 | A1* | 12/2013 | Boyden | A61B 5/686 623/8 |
| 2017/0181825 | A1* | 6/2017 | Hunter | A61B 5/4312 |
| 2017/0228627 | A1* | 8/2017 | Geissler | A61B 5/0031 |
| 2018/0014747 | A1 | 1/2018 | Akselrod | |

FOREIGN PATENT DOCUMENTS

| | | | | |
|---|---|---|---|---|
| CN | 114630615 | | 6/2022 | |
| WO | 2017137853 | | 8/2017 | |
| WO | 2017196973 | | 11/2017 | |
| WO | WO-2017196973 | A2 * | 11/2017 | B29C 33/424 |
| WO | 2021064686 | | 4/2021 | |

OTHER PUBLICATIONS

International Search Report for PCT/IB2020/059287, dated Jan. 14, 2021, (4 pages).
Luo, L. et al., "Detection and Prediction of Ovulation from Body Temperature Measured by an In-Ear Wearable Thermometer," *IEE Transaction on Biomedical Engineering*, pp. 1-11 (2019).
Maijala, A. et al., "Nocturnal finger skin temperature in menstrual cycle tracking: ambulatory pilot study using a wearable Oura ring," *BMC Women's Health*, vol. 19, No. 150, pp. 1-10 (2019).
Owen, "Physiological signs of ovulation and fertility readily observable by women," *The Linacre Quarterly*, vol. 80, No. 1, pp. 17-23 (2013).
Rao, K.H.S. et al., "Computer Assisted Thermography and its Application in Ovulation Detection," Institut de Microtechnique, Maladière-71, pp. 459-464 (1984).
Regidor, P. et al., "Identification and prediction of the fertile window with a new web-based medical device using a vaginal biosensor for measuring circadian and circamensual core body temperature" Gynecological Endocrinology, pp. 1-5 (2017).
Shah et al., "Determination of fertility interval with ovulation time estimation using differential skin surface temperature (DST) measurement," Communications-in-Brief: Fertility and Sterility, vol. 41, No. 5, pp. 771-774 (1984).
Shilaih, M. et al., "Modern fertility awareness methods: wrist wearables capture the changes in temperature associated with menstrual cycle," *Bioscience Reports*, vol. 38 BSR20171279, pp. 1-12 (2018).
Veetil, P.M., "Implantable Wireless Sensor Networks: Application to Measuring Temperature for In Vivo Detection of Infections," Dissertations, Master's Theses and master's Reports, Michigan Technological University, 2017, available at https://digitalcommons.mtu.edu/cgi/viewcontent.cgi?article=1408&context=etdr.
Yang et al., "Literature Survey on Biomedical Applications of Thermography," *Bio-Medical Materials and Engineering*, vol. 2, pp. 7-18 (1992).
"International Application Serial No. PCT IB2020 059287, International Search Report mailed Jan. 14, 2021", 3 pgs.
"International Application Serial No. PCT IB2020 059287, Written Opinion mailed Jan. 14, 2021", 7 pgs.
"International Application Serial No. PCT IB2020 059287, International Preliminary Report on Patentability mailed Apr. 14, 2022", 9 pgs.
"European Application Serial No. 20793154.4, Response to Communication Pursuant to Rules 161 and 162 EPC filed Nov. 18, 2022", 15 pgs.
"Canadian Application Serial No. 3,156,319, Examiners Rule 86(2) Report mailed Nov. 3, 2023", 5 pgs.
"European Application Serial No. 20793154.4. , Communication Pursuant to Article 94(3) EPC mailed Jan. 23, 2025", 11 pgs.
"European Application Serial No. 20793154.4, Communication Pursuant to Article 943 EPC mailed Mar. 18, 2026.", 7 pgs.

* cited by examiner

METHODS AND SYSTEMS FOR SENSING PARAMETERS IN IMPLANTABLE DEVICES

CROSS-REFERENCE TO RELATED APPLICATIONS

This application is the U.S. national phase entry under 35 U.S.C. § 371 of International Application No. PCT/IB2020/059287, filed on Oct. 2, 2020, which claims priority to U.S. Provisional Application No. 62/909,318, filed on Oct. 2, 2019, which is incorporated by reference herein in its entirety.

TECHNICAL FIELD

The present disclosure relates to medical applications of sensing technology (e.g., temperature, pressure, motion, etc.) in implantable medical devices, implants incorporating such technology, and methods of use thereof.

BACKGROUND

Implantable medical devices may be implanted into patients for a variety of reasons, including, for example, to improve a clinical condition, to replace natural patient tissue, or for aesthetic purposes. For example, tissue expanders and breast implants may be used in reconstructive surgeries following mastectomy, cancer, surgical removal of breast tissue, radiation therapy, or other medical treatment that damages, destroys, or removes natural breast tissue. Such implantable medical devices often need to be examined, monitored, identified, or further altered after implantation. The tissue around the implantable device may also need to be examined, monitored, and potentially treated, after implantation.

For example, after implantation of a medical device, follow-up may be helpful to monitor healing, check for change in clinical condition, and/or screen for development or reappearance of other medical conditions in tissue proximate to the implanted device. Further, some implantable medical devices may require adjustment after implantation. For example, tissue expanders are typically designed to be incrementally expanded over time in order to prepare for insertion of another implant.

Various technologies have been developed in order to improve the efficacy of implantable medical devices. Among these technologies is the use and integration of transponders, such as radio-frequency identification (RFID) transponders. However, transponders within implantable medical devices may interfere with the use of certain diagnostic, imaging, or other medical techniques on patients having implants including transponders. For example, ferromagnetic components may interfere with magnetic resonance imaging (MRI) of the patient.

SUMMARY

The present disclosure includes implantable transponders comprising features that may provide for increased safety, compatibility with medical imaging technology and/or other procedures, and decreased necessity for invasive procedures. While portions of the disclosure refer to breast implants and tissue expanders, the devices, systems, and methods disclosed herein may be used with other implantable medical devices, such as, for example, other implants used in cosmetic and/or reconstruction procedures.

Medical implants described herein include a flexible shell and a plurality of sensors. The flexible shell may include a base. The plurality of sensors may be incorporated onto and/or into the shell, e.g., between layers of the base or other portion of the shell. That is, for example, the plurality of sensors may be incorporated into the base. Optionally, the base may have a uniform thickness and/or a thickness greater than the thickness of the remainder of the shell. The plurality of sensors may be distributed at different locations of the shell. According to some aspects of the present disclosure, one or more sensors, e.g., each sensor, of the plurality of sensors is equidistant from a center of the base. For example, the plurality of sensors may include a sensor at or proximate a center of the base and two or more sensors equidistant from the center of the base.

One or more sensors, e.g., each sensor, of the plurality of sensors may be configured to measure a parameter such as temperature and/or pressure. Further, for example, each sensor may be configured to transmit data at a frequency different from the frequency of one or more of the other sensors, may be configured to transmit data at a time different from the time data is transmitted by one or more of the other sensors, and/or may include a device identifier different from the device identifier of one or more of the other sensors. In at least one example, each sensor is configured to transmit data at a frequency different from the frequency of each of the other sensors, is configured to transmit data at a time different from the time data is transmitted by each of the other sensors, and/or includes a device identifier different from the device identifier of each of the other sensors. The plurality of sensors may include, for example, at least two, three, four, five, or six or more sensors.

Each sensor may comprise an electromagnetic coil. For example, each sensor may include an application-specific integrated circuit coupled to the electromagnetic coil, the integrated circuit optionally being disposed at or proximate the center of the electromagnetic coil, wherein the integrated circuit is configured to measure the parameter such as, e.g., temperature, pressure, and/or other parameter(s) as described herein. Further, each sensor may include an enclosure around the electromagnetic coil and/or integrated circuit, optionally wherein the enclosure comprises glass or a ceramic. Each sensor may have a cylindrical or rectangular shape, for example.

The implant may further include one or more radiopaque markers, optionally wherein the radiopaque marker(s) are coupled to or integrated into an anterior side of the shell opposite the base; and/or one or more tabs for securing the implant to tissue. According to some aspects of the present disclosure, the implant is a breast implant or a tissue expander. For example, the implant may be a tissue expander with a port configured to receive and evacuate a fluid, optionally wherein the port includes a transponder in communication with each sensor of the plurality of sensors of the tissue expander.

According to some aspects of the present disclosure, each sensor of the plurality of sensors transmits data at a frequency between about 100 kHz and about 250 kHz, such as between about 120 kHz and about 150 kHz. In at least one example, the plurality of sensors includes at least four sensors, which include a first sensor in a superior portion of the shell; a second sensor in a first lateral portion of the shell; a third sensor in a second lateral portion of the shell, where the first lateral portion is on the opposite side of a vertical plane bisecting the implant, from the second lateral portion;

and a fourth sensor in an inferior portion of the shell. According to some aspects, the implant does not include ferromagnetic materials.

The present disclosure also includes systems comprising an implant as described above and/or elsewhere herein and a reader (e.g., an external reader) in communication with the plurality of sensors. The reader may be configured to be handheld and/or incorporated into an article of clothing or an accessory. For example, the present disclosure includes a system that includes a medical implant and a reader. The medical implant may comprise a flexible shell including a base and a plurality of sensors incorporated into the base (such as, e.g., between layers of the base). The plurality of sensors may include at least three sensors spaced apart, each sensor comprising an electromagnetic coil and being configured to measure and/or transmit data (such as, e.g., temperature and/or pressure data) to the reader. For example, each sensor may include an application-specific integrated circuit coupled to the electromagnetic coil. The reader may be in communication with each sensor of the plurality of sensors. The reader may be configured to receive the data and communicate the data to a server, such as a remote server. In at least one example, each sensor of the plurality of sensors is configured to transmit data to the reader at a frequency different than a frequency of the other sensors, each sensor of the plurality of sensors is configured to transmit data to the reader at a time different from a time the other sensors, and/or each sensor of the plurality of sensors is configured to transmit data to the reader that includes a device identifier different from the device identifier of the other sensors The present disclosure also includes methods of manufacturing medical implants and methods of using medical implants. For example, a method of manufacturing an implant comprising a plurality of sensors and a flexible shell that includes a base may comprise coupling the plurality of sensors to an external portion of the shell. Each sensor may include an electromagnetic coil and an enclosure, each sensor being configured to measure a parameter such as temperature and/or pressure. For example, each sensor may include an application-specific integrated circuit coupled to the electromagnetic coil. The method may further comprise sealing the base to the external portion of the shell, such that the plurality of sensors is incorporated into the shell, e.g., incorporated into the base. The plurality of sensors may be distributed at different locations of the shell. Sealing the base may include vulcanizing the base to the external portion of the shell. Optionally, the base includes an indentation corresponding to a location of each sensor. Thus, for example, the base with the plurality of sensors incorporated therein may have a uniform thickness.

The present disclosure also includes methods of obtaining information for a patient having an implant, the implant comprising a flexible shell and a plurality of sensors distributed at different locations of the implant. The method may include transmitting data from the plurality of sensors to an external reader configured to communicate the data to a cloud-based server, wherein each sensor transmits data at a frequency different from a frequency of one or more of the other sensors; at a time different from a time data is transmitted by one or more of the other sensors; and/or that includes a device identifier different from the device identifier of one or more of the other sensors. The plurality of sensors may be incorporated into the shell of the implant. For example, the posterior side of the implant may include a base, wherein the plurality of sensors are incorporated into the base. In some examples, the implant is a breast implant or a tissue expander.

The data may be transmitted continuously and/or at period intervals. For example, the data may be transmitted at periodic intervals ranging from about 1 minute to about 6 hours, such as from about 5 minutes to about 3 hours, or from about 15 minutes to about 1 hour. According to some aspects of the present disclosure, the data may be transmitted to the external reader when the external reader is within about 10 feet, about 5 feet, or about 2 feet of the implant and/or of the respective sensors. The reader may be a handheld device and/or may be incorporated into an article of clothing or an accessory. The data transmitted by the plurality of sensors may include a temperature of an area of patient tissue proximate each sensor of the plurality of sensors, for example. The data may provide information about a status of patient tissue surrounding the implant, and/or information about a health condition of the patient. In at least one example, the data provides information about a fertility cycle of the patient (e.g., via temperature information).

It is to be understood that both the foregoing general description and the following detailed description are exemplary and explanatory only and are not restrictive of the claims.

BRIEF DESCRIPTION OF THE DRAWINGS

The accompanying drawings, which are incorporated in and constitute a part of this application, illustrate various examples and together with the description, serve to explain the principles of the present disclosure. Any features of an embodiment or example described herein (e.g., device, system, method, etc.) may be combined with any other embodiment of example, and are encompassed by the present disclosure.

DETAILED DESCRIPTION

Figure 1:
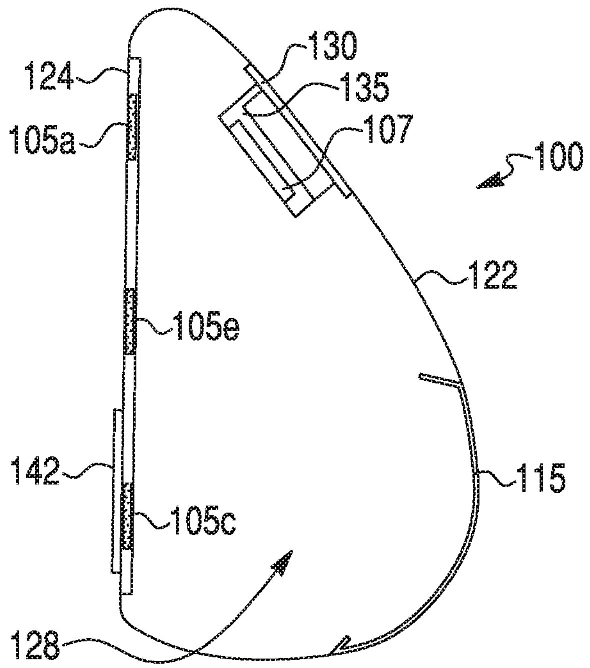
FIGS. 1-3 show an implant including a plurality of sensors, according to some aspects of the present disclosure.

Aspects of the present disclosure are described in greater detail below. The terms and definitions as used and clarified herein are intended to represent the meaning within the present disclosure. If in conflict with terms and definitions incorporated by reference, the terms and definitions provided herein control.

The singular forms "a," "an," and "the" include plural reference unless the context dictates otherwise. The terms "approximately" and "about" refer to being nearly the same as a referenced number or value. As used herein, the terms "approximately" and "about" generally should be understood to encompass ±5% of a specified amount or value.

As used herein the term "posterior" refers to the back of a patient and the term "anterior" refers to the front of a patient. Thus, for example, the posterior side of a breast implant or tissue expander is the side of the implant facing the chest wall, while the anterior side is the opposite side closest to the skin. Similarly, the posterior side of a gluteal or buttock implant or tissue expander is the side closest to the skin, and the anterior side is the opposite side, facing the pelvis. "Superior" refers to the top of the patient, i.e., the direction towards the head of the patient. "Inferior" refers to the bottom of the patient, i.e., the direction towards the feet of the patient. "Medial" refers to being towards or near to the median or center line of an implant. For example, a medial portion of the implant may be the portion of the implant closest to a vertical plane symmetrically bisecting the implant. "Lateral" may refer to being towards one of the peripheral side of the implant, for example, the left or right sides of the implant. A lateral portion of the implant may refer to a peripheral portion of the implant on either side of the aforementioned vertical plane (e.g., a left portion or a right portion).

Examples of the present disclosure may provide for non-invasive systems and methods for obtaining information about an implant within a patient's body and/or about the patient, including, but not limited to, detecting status information about an implant and/or the tissue surrounding the implant. Some examples of the present disclosure may allow for early detection and/or continuous monitoring of implant status, complications, and/or aberrations. In some instances, changes in temperature may relate to the status of patient tissue, such as inflammation, infection, or atypical cell growth in tissues surrounding the implant. Early detection of such complications (e.g., by early detection of temperature changes in surrounding tissue) may allow for early diagnosis and/or treatment. Changes in temperature may be indicative of other conditions, such as fertility.

Implants of the present disclosure may include a plurality of sensors, where each sensor of the plurality of sensors may be spaced at a fixed location apart from the other sensors, such that each sensor provides information regarding a distinct region of the implant, and/or a distinct region of tissue proximate to a portion of the implant including the sensor. The implants including a plurality of sensors (e.g., implants comprising a multi-sensor array) may assist in detecting temperature changes in a specific region of tissue and/or a specific region of the implant that may indicate an abnormality in the implant, a potential adverse tissue reaction, or other potential complication. In some embodiments, detection of temperature changes and/or monitoring of temperature trends over time may allow for tracking of hormonal cycles related to fertility and/or pregnancy.

Although the methods and systems herein primarily refer to temperature measurements and sensors configured to measure temperature, it should be understood that the present disclosure includes implantable medical devices configured to monitor other physiological parameters. For example, the sensors described herein may be configured to monitor changes in pressure, motion, cyclo-rotation, amplitude and/or frequency of mechanical waves (e.g., acoustics), electromagnetic frequency, electromagnetic intensity (e.g., light intensity), and/or other parameters or conditions that may be indicative of patient health status and/or status of the implant.

Exemplary systems and methods according to the present disclosure may include one or more sensors located on, incorporated into, or disposed adjacent to a shell of an implant, such as a tissue expander or breast implant. One or more sensors may be disposed on, incorporated into, or disposed adjacent to any other part of the implant (e.g., within a filling material or other interior of a breast implant). In some instances, the sensor(s) may measure an average temperature of the immediate area of the respective sensor(s), including the average temperature of portions of tissue surrounding the implant. As an example, there may be several temperature sensors (e.g., two, three, four, five, or six or more) on or in an implant such as a tissue expander, allowing for temperature measurement at different places around the implant (e.g., temperature measurement at multiple different localized areas of tissue adjacent to the sensors).

Each sensor may include an application-specific integrated circuit (ASIC) configured to detect and/or measure the desired parameter, such as temperature (e.g., a temperature chip). The ASIC may include, or may be in communication with, an RFID circuit and/or a printed circuit board. According to some aspects, one or more sensors may include a transponder comprising an electromagnetic coil coupled to an ASIC. In some embodiments, one or more sensors include an ASIC having a built-in capacitor.

According to some aspects of the present disclosure, the sensors may include and/or may be in communication with an antenna, e.g., an electromagnetic coil, providing for wireless communication. For example, one or more sensors of the implant may include and/or may be in communication with an RF coil, optionally a non-ferromagnetic RF coil, allowing for the transmission and/or receipt of data. Thus, for example, the sensor may be configured as a transponder. The electromagnetic coil may comprise a conductive material such as copper or other non-ferromagnetic metal. For example, the coil may comprise a wire wrapped around a non-conductive biocompatible polymer (e.g., poly-ether-ether-ketone (PEEK)) or configured into a coil surrounding air or other inert gas. The sensors according to the present disclosure may include an ASIC coupled to the electromagnetic coil (e.g., via wires), optionally wherein the ASIC is disposed within the center of the electromagnetic coil.

Each sensor may have a communication range of approximately 1 inch to approximately 10 feet, such as about 1.5 inches to about 6 feet, about 2 inches to about 3 feet, or about 1 inch to about 5 feet. The sensors herein include circuitry that assists in filtering noise from raw data, or otherwise improving the signal-to-noise ratio of the transmitted implant data. For example, the sensors may include chips programmed with algorithms for include filtering, collating, organizing, and/or analyzing data. Such algorithms may be designed to combine relevant integrated data specific to provide a proper signal indicative of a physiological parameter of the patient, such as information about the tissue surrounding the implant, and/or a characteristic of the implant.

According to some aspects of the present disclosure, each sensor may transmit at a frequency between about 100 kHz and about 400 kHz, such as between about 100 kHz and about 200 kHz, between about 120 kHz and about 150 kHz, or between about 125 kHz and about 134 kHz. For example, the frequency of each sensor (which may be the same or different from one or more other sensors of the implant) may be about 100 kHz, about 110 kHz, about 120 kHz, about 125 kHz, about 130 kHz, about 135 kHz, about 140 kHz, about 150 kHz, about 160 kHz, about 170 kHz, about 180 kHz, about 190 kHz, or about 200 kHz. One or more sensors may transmit at a frequency different from one or more other sensors of the implant. For example, each sensor may transmit at a frequency different from the frequency of each of the other sensors, such that each sensor transmits at a unique frequency. Thus, in an example, the implant may include at least two sensors that transmit at a frequency at least 0.1 kHz, at least 0.2 kHz, at least 0.3 kHz, at least 0.5 kHz, at least 1 kHz, at least 1.5 kHz, or at least 2 kHz different from each of the other sensors. The difference in frequency among all sensors may range from about 0.1 kHz to about 20 kHz, such as from about 0.2 kHz to about 1 kHz, from about 0.5 kHz to about 5 kHz, about 0.5 kHz to about 3 kHz, or about 2 kHz to about 10 kHz. In at least one example, the implant includes a plurality of sensors transmitting at different frequencies ranging from about 100 kHz to about 150 kHz, wherein the frequency of each sensor differs from the frequency of one or more other sensors, e.g., each other sensor, by about 0.1 kHz to about 20 kHz, such as about 1 kHz to about 10 kHz, about 2 kHz to about 5 kHz, about 3 kHz to about 8 kHz, or about 5 kHz to about 15 kHz.

In some examples of the present disclosure, a sensor may transmit at the same frequency as one or more other sensors (including any of the frequencies listed above). Sensors transmitting at the same frequency may be configured to transmit at different rates and/or at different times, such as in an offset synchronized fashion (e.g., exhibiting a time delay between transmissions by one sensor and by another sensor), such that information transmitted by one sensor does not interfere with information being transmitted by another sensor.

In addition or as an alternative to transmitting at different or unique frequencies, the sensors herein may have different identifying information. For example, each sensor may have a unique device identifier useful for associating the sensor with the data obtained by that sensor. Information provided by the unique device identifier may include, e.g., one or more serial number(s), manufacturer name(s), date(s) of manufacture, and/or lot number(s).

The sensors may be configured so that are not palpable on or though the exterior, e.g., shell, of the implant, regardless of the position of the implant and patient. The sensors herein may comprise an enclosure, such as, for example, a vial, capsule, pouch, or other enclosure disposed around the electronic components of the sensor (e.g., ASIC, electromagnetic coil, etc.). The enclosure may be disposed within or otherwise coupled to the implant. The enclosure may help to protect the electronic components, such as providing for heat and/or shock resistance. In addition or alternatively, the enclosure may be configured to restrict components of the sensor from separating or moving apart. The enclosure may comprise a material or combination of materials such as, for example, a polymer such as PEEK or other plastic, or silicone; a ceramic, aluminum and alloys thereof, and/or glass. Optionally, the enclosure may be coated with silicone or other biocompatible material.

The interior of the enclosure around the electronic components may include a material that does not interfere with the operation of the components contained within the enclosure. For example, a portion of the sensor within the enclosure may comprise air or other inert gas. The sensors herein may have any suitable shape such as, e.g., cylindrical, ovoid, rectangular, cubic, among other possible shapes. The sensors may have dimensions ranging from about 2 mm to about 30 mm (width, length, and/or height). In at least one example, one or more sensors has a length ranging from about 3 mm to about 15 mm, e.g., from about 9 mm to about 12 mm; and a width ranging from about 5 mm to about 10 mm, e.g., from about 4 mm to about 6 mm. In some examples, the length may be equal to the width, and the height may range from about 1 mm to about 6 mm, such as from about 2 mm to about 5 mm.

The electronic components of a given sensor may be in operable communication with the electronic components of one or more other sensors or other transponders of the implant, and/or may be in operable communication with a reader external to the implant and the patient. For example, an exemplary implant may include a first sensor in wireless communication with a second sensor disposed at or coupled to a different location of the implant. As described below, one or more sensors may transmit data to a reader. In some aspects of the present disclosure, the implant may include a plurality of sensors in communication with a single transponder of the implant (wherein the transponder does or does not include an ASIC configured to detect or measure parameters), and the transponder may relay data from the sensors to the reader. Such transponders may include any of the features of transponders disclosed in WO 2017/137853, which is incorporated by reference herein in its entirety. Further, any tissue expander according to the present disclosure may include an integrated port as disclosed in WO 2017/137853, which is incorporated by reference here in its entirety, for receiving and expelling a fluid during expansion and contraction of the tissue expander.

As mentioned above, in some aspects of the present disclosure, the sensors may be located on, incorporated into, or disposed adjacent to, a shell of the implant. For example, the implant may include a polymer shell, e.g., comprising an elastic material such as a biocompatible silicone, e.g., polydimethylsiloxane, wherein each sensor may be coupled to an inner surface, an outer surface, or incorporated into a wall of, the shell. In some examples, the sensors are incorporated into the thickness of the shell wall. In such cases, the distance between each sensor and the outermost surface of the shell may be less than or equal to the thickness of the shell. The total thickness of the shell may range from about 0.1 mm to about 1.5 mm, such as from about 0.2 mm to about 0.8 mm, from about 0.3 mm to about 1.1 mm, or from about 0.4 mm to about 0.6 mm. In some examples, the thickness of the shell may range from about 0.3 mm to 1.0 mm, e.g., a thickness of about 0.4 mm, about 0.5 mm, about 0.6 mm, about 0.7 mm, about 0.8 mm, about 0.9 mm, or about 1.0 mm. The shell may have a generally uniform thickness, or portions of the shell may vary in thickness. For example, in the case of a tissue expander for implantation in breast tissue, the posterior side of the implant may have a relatively greater thickness than the anterior side in order to promote expansion in the anterior direction. In at least one example, the posterior side of the implant (also referred to herein as the base of a tissue expander) includes two or more sensors incorporated into the shell. Sensors disposed at or proximate the anterior side of the implant may allow for measuring temperature and/or other parameters of tissue towards the chest wall of a patient. Sensors may be incorporated into other portions of the shell including, e.g., the anterior side. Sensors disposed at or proximate the posterior side of the implant may allow for measuring temperature and/or other parameters of tissue towards the skin of the patient. In some examples, one or more sensors may be disposed within the cavity of an implant, e.g., incorporated into filling material such as saline solution or silicone gel, to provide information about the filling material and/or other conditions within the interior of the implant.

Where an implant includes a plurality of sensors, each sensor may be spaced at a fixed location apart from the other sensors, such that each sensor provides information regarding a distinct region of the implant, or distinct region of tissue proximate to the implant. In some embodiments, sensors may measure a signal (e.g., an impedance signal) between two or more sensor(s) and/or transponder(s). This impedance signal may be used to generate data indicative of a physiological condition of the patient. The sensor(s) and/or transponders may be configured to assist in determining a location and/or orientation of an implant. For example, based on relative locations, relative signal strengths, communication with a reference (e.g., a reference electrode or reference transponder), and/or signals between sensors and transponders, a location and/or orientation of the implant containing the sensors and/or transponders may be determined.

An exemplary implant according to the present disclosure may include at least four sensors: a first sensor in a superior portion of the implant; a second sensor in a first lateral portion (e.g., a left portion) of the implant; a third sensor in a second lateral portion (e.g., a right portion) of the implant, where the first lateral portion is opposite the second lateral portion; and a fourth sensor in an inferior portion of the implant. Other examples may include fewer or more sensors.

Providing sensors at fixed locations in different portions of an implant allows for measurements (e.g., pressure and/or temperature measurements) to be taken at multiple locations around the implant. The several measurements may provide more localized and precise information to assist a healthcare professional to evaluate the health status of the patient and integrity of the implant. For example, an infection or abnormal tissue reaction to an implant may correspond to a change in temperature and/or other parameter detected or measured by sensors proximate the affected tissue. Therefore, an aberration or atypical pattern exhibited by one or more sensors may indicate which portions of the implant are near the source of aberration or atypicality.

The implants herein optionally may include one or more features to further assist with imaging and/or securing the implant within patient tissue. For example, the implant may include one or more radiopaque markers visible by imaging, for example, to assist in monitoring the location, position, and/or orientation of the implant over time. The radiopaque marker(s) may be in the shape of stripes, crosses, an "I" configuration, or other shapes with identifiable orientations. Additionally or alternatively, the implant may include one or more tabs integrated into or coupled to the outermost surface of the implant. For example, the base of a breast implant or tissue expander may include one or more, e.g., two, three, four, five, or six or more tabs. The tabs may be arranged at different radial positions and allow for securing of sutures to tissue of the chest wall, e.g., via an aperture of each tab.

Figure 2:
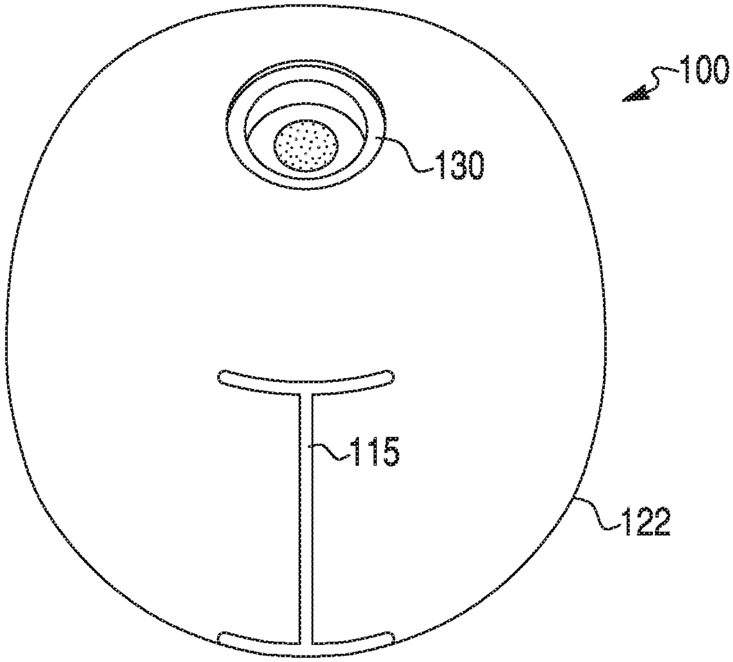
Figure 3:
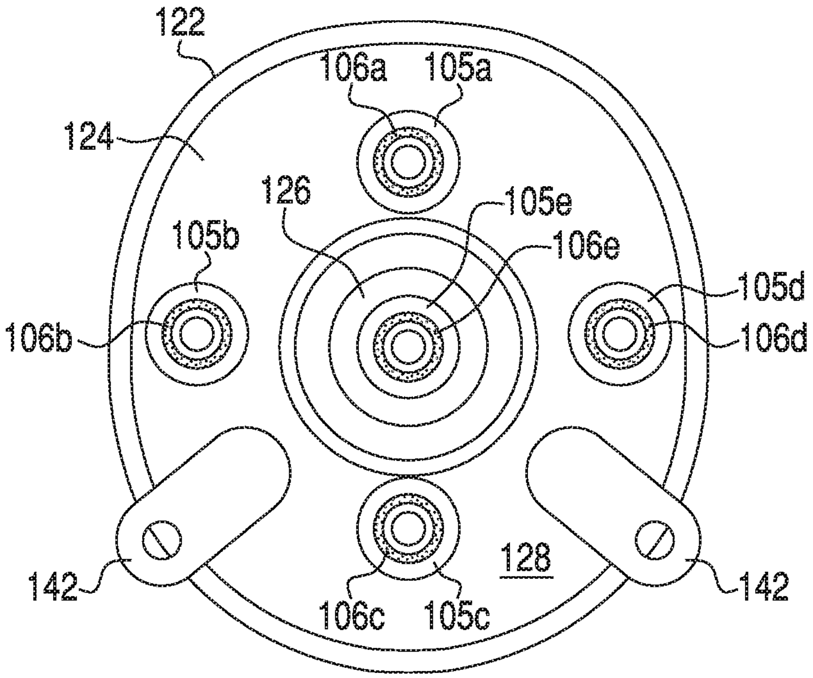

Reference will be made an implant 100 shown in FIGS. 1-3 to illustrate exemplary features of the present disclosure. The implant 100, shown as a tissue expander, is exemplary only and non-limiting of the scope of the present disclosure. Tissue expanders are generally useful to stretch or promote expansion of tissue in a patient in preparation for a permanent implant. FIG. 1 is a side cross sectional view of the implant 100, FIG. 2 is an anterior view, and FIG. 3 is a posterior view. It should be understood that aspects described in relation to one or more of the figures does not limit that aspect to the devices shown in the discussed figures. Rather the all of figures should be view in context of the entire application, and as describing various aspects that may optionally be incorporated in the implants described herein. The components and aspects of the implants described herein may be used in any arrangement or combination that allows for the measurement of one or more parameters (e.g., temperature) at multiple locations of an implant.

Referring to FIGS. 1-3, the implant 100 as shown comprises a shell 122 that includes a base 124 and a patch 126, wherein the shell 122 defines a cavity or interior 128 of the implant 100. Tabs 142 coupled to the base 124 may facilitate securing the implant 100 to tissue. The implant 100 also includes a plurality of sensors **105*a*-105*e* (each sensor 105*a*-105*e* including, e.g., one or more ASIC(s) and electromagnetic coil(s) 106*a*-106*e*) and a radiopaque marker 115**.

The implant 100 includes an injection port 130 through which a fluid may be introduced and removed from the interior 128 of the implant 100 to expand and contract its volume. Port includes a transponder 135 (e.g., having a unique device identifier) with electromagnetic coil 107. The port 130 may be, for example, an integrated port as disclosed in WO 2017/137853, which is incorporated by reference here in its entirety. By having a transponder 135, a healthcare professional may be able to noninvasively identify the appropriate location of port 130 for introducing and removing fluid. The implants herein need not include a port, such as, e.g., permanent implants (e.g., breast implants, gluteal implants, etc.).

Shell 122 may define a cavity therein, an expandable cavity in the case of tissue expander implant 100. The cavity is referred to in FIG. 1 as interior space 128. Implant 100 also includes a base 124, which forms the anterior side of shell 122. Base 124 may have a generally round shape, an ovular shape, or a teardrop shape, for example. The base may be an integral part of shell 122 or may be coupled to the remainder of shell 122 by vulcanization or with an adhesive.

As mentioned above, positioning a plurality of sensors **105*a*-105*e* within base 124 may allow for the sensors 105*a*-105*e* to measure a temperature and/or determine a condition of patient tissue towards the chest wall. Further, placing the sensors 105*a*-105*e* at different locations, e.g., different quadrants, of base 124 may allow for measurements (e.g., temperature) to be taken that are representative of several regions of tissue. For example, referring to FIG. 3, a first sensor 105*a* may transmit data corresponding to tissue proximate a superior portion of implant 100, a second sensor 105*b* may transmit data corresponding to tissue proximate a first lateral portion (e.g., a left portion) of implant 100, a third sensor 105*c* may transmit data corresponding to tissue proximate an inferior portion of implant 100, a fourth sensor 105*d* may transmit data corresponding to tissue proximate a second lateral portion (e.g., a right portion) of implant 100, and a fifth sensor 105*e* may transmit data corresponding to tissue proximate a middle (e.g., central) portion of implant 100. The fifth sensor 105*e* may be integrated into the patch 126, and optionally may provide information regarding the condition of the implant near the patch 126 (e.g., the integrity of the seal) and/or tissue proximate the patch 126**.

The drawings show some exemplary distributions and positionings of sensors **105*a*-105*e*. However, any distribution of sensors is contemplated that allows for the collection of data (e.g., measuring of temperature) at various points along the exterior of implant 100. For example, one or more sensors may be incorporated into portions of base 124 proximate to tabs 142, enabling a condition (e.g., temperature) of tissue near tabs 142** to be assessed.

In some embodiments, each sensor **105*a*-105*e* has a unique transmission frequency and/or unique device identifier, indicating to the healthcare professional via a reader which sensor 105*a*-105*e* (and which portion of the implant 100) is associated with which measurements. For example, each sensor 105*a*-105*e* may transmit data including the parameter (e.g., temperature) on a unique frequency and/or with a unique device identifier (e.g., serial number, etc.). The unique frequency and/or device identifiers associated with the respective sensors, in combination with their known positions within different portions of implant 100**, may allow a healthcare professional or other user to better evaluate the status of the patient and the implant.

The sensors 105*a*-105*e* and/or transponder 135 in communication with the sensors 105*a*-105*e* are shown incorporated into base 124 and patch 126 of shell 122. In other examples, sensors may be coupled to the innermost or outermost surface of shell 122 and/or incorporated into the interior or other structure of an implant. For example, one or more sensors may be attached or encased in a suitable material such as silicone dielectrically sealed or bonded to the shell.

Sensors 105*a*-105*e* and transponder 135 may be positioned to avoid interference with each other and/or avoid interference with the introduction and removal of fluid from port 130. Each sensor 105*a*-105*e* and port 130 may comprise non-ferromagnetic materials, such that implant 100 does not include ferromagnetic materials. By being non-ferromagnetic, implant 100 may avoid interference with imaging technologies used for screening (e.g., MRI, fluoroscopic imaging, and/or ultrasound imaging).

The implants disclosed herein may be produced using any suitable manufacturing process. For example, shells of implants according to some aspects of the present disclosure, such as, for example, shell 122, may be produced by dip-molding For example, a mandrel may be used as a mold and dipped, e.g., at least partially or fully submerged in a thermoplastic or thermosetting material, such as a silicone dispersion, such that the silicone material at least partially or fully coats a surface of the mandrel. The mandrel may be repeatedly dipped in order to form a multilayer shell. The mandrel may have an imprint to provide the shell and outermost surface of the implant with a biocompatible surface features and characteristics. The implants herein may include any of the surface features and characteristics thereof disclosed in WO 2017/196973 and/or WO 2015/121686, both of which are incorporated by reference in their entireties.

After or during the formation of an implant shell, one or more sensors may be affixed to or integrated into the shell, for example, by adhesive, vulcanization, dielectric bonding, or other type of thermoplastic integration.

Each layer of shell 122 may have the same or different composition with respect to the other layer(s). For example, while forming shell 122, mandrel may be dipped in different materials, e.g., silicone dispersions having different viscosities and/or different types of additives. In some examples, the shell 122 may include one or more barrier layers to inhibit or prevent the passage of liquid or gel materials through the shell 122. One or more layers of shell 122 may comprise, for example, diphenyl silicone elastomers, dimethyl silicone elastomers, diphenyl-dimethyl silicone elastomers, methyl phenyl silicone elastomers, fluorinated silicone elastomers such as trifluoropropyl silicone elastomers, and combinations thereof. One or more layers of shell 122 may be colored, for example, by adding one or more pigments to the thermoplastic or thermosetting material the mandrel is being dipped into. For example, pigment may be included in a barrier layer to facilitate examination of the continuity and/or integrity of the barrier layer(s).

Once the appropriate number of layers have formed around the mandrel, the thermoplastic and/or thermosetting material(s) may be allowed to cure. Shell 122 may be cured at a temperature ranging from about 100° C. to about 200° C., such as, for example, about 125° C. to about 150° C. In some examples, the curing temperature may range from about 125° C. to about 127° C., e.g., about 125° C., about 126° C., or about 127° C. In further examples, the curing temperature may be about 150° C. The cured shell 122 may be removed from the mandrel and inverted or turned inside out. Thus, the surface of the shell 122 formerly in contact with the mandrel forms the exterior surface of the shell 122. Alternatively, the cured shell may be removed from the mandrel and not be turned inside out.

Base 124 may be formed by a molding technique, such as, for example, injection molding or pour molding. Base 124 may include indentations or depressions corresponding to the positions or locations desired for the sensors 105*a*-105*e*, allowing for the sensors 105*a*-105*e* to be incorporated into the wall of base 124 and for base to have a uniform thickness even when sensors 105*a*-105*e* are incorporated therein. This also may facilitate gathering data by the sensors 105*a*-105*e* of tissue surrounding the implant 100, as less material may be disposed between the sensors 105*a*-105*e* and the surrounding tissue. Thus, in some examples, a mold used to form base 124 may include protrusions that provide corresponding indentations or depressions for receiving sensors 105*a*-105*e*. After or during curing of base 124, the sensors 105*a*-105*e* may be affixed to base 124 at the desired positions or locations (e.g., within the indentations or depressions).

After base 124 is formed and sensors 105*a*-105*e* disposed at the desired positions and locations, base 124 may be bonded or otherwise sealed to the remainder of shell 122. For example, the base 124 may be vulcanized to shell 122 such that the entire edge surface of base 124 (e.g., the surface between an interior surface of base 124 and an exterior surface of base 124) is bonded to the remainder of shell 122.

The base 124 may include a patch 126 comprising the same or a similar material as the remainder of shell 122, wherein patch 126 covers the opening left by the mandrel (e.g., a handle of the mandrel). Patch 126 may be vulcanized or otherwise coupled or bonded to base 124 and/or the remainder of shell 122. Optionally, the patch 126 may include one or more sensors incorporated therein, and/or one or more sensors may be coupled to an inner surface and/or outer surface of patch 126.

Figure 4:
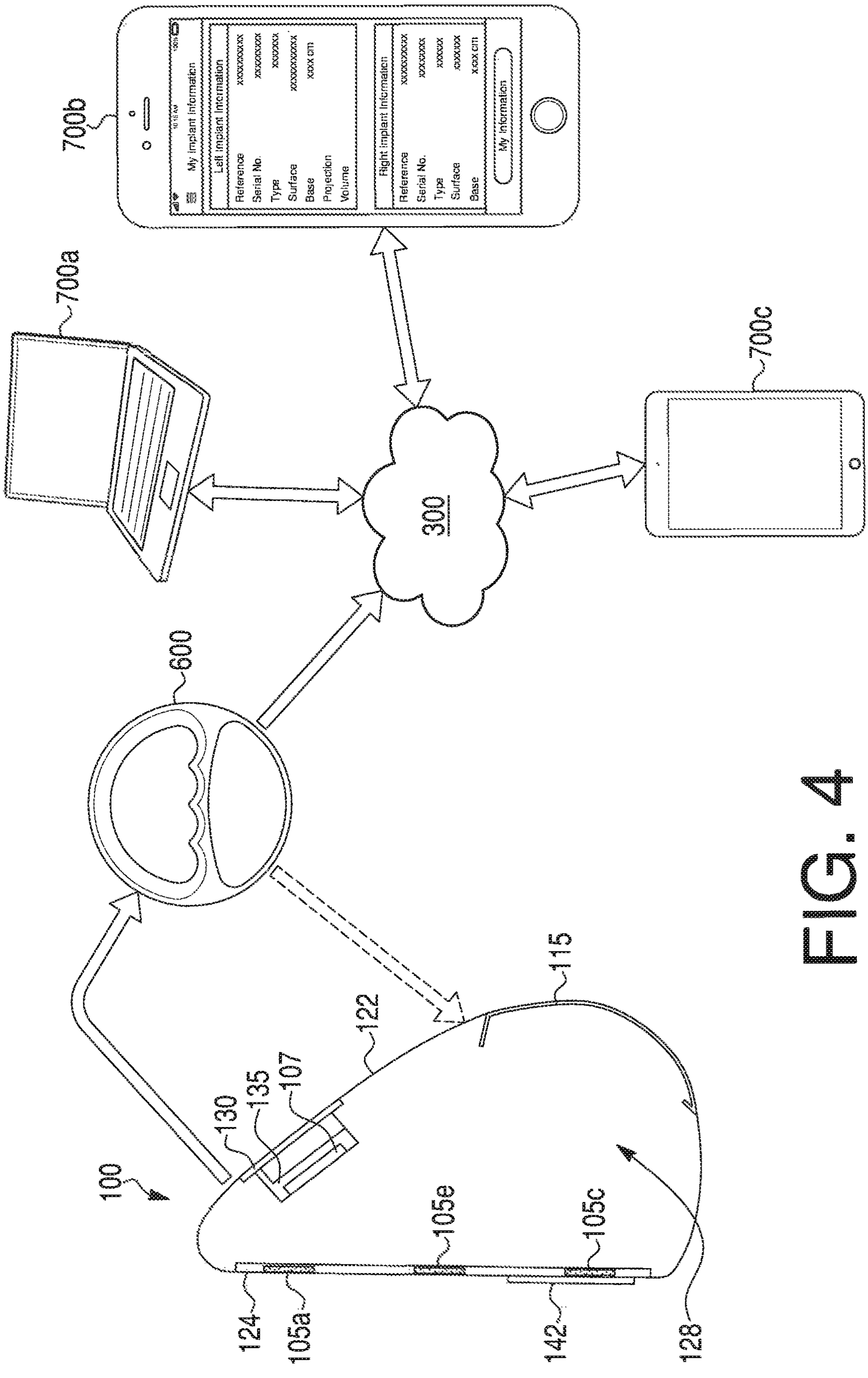
FIG. 4 is a diagram of an exemplary system for obtaining, recording, and/or analyzing implant data, according to some aspects of the present disclosure.

Referring to FIG. 4, a system for monitoring, recording, tracking, or analyzing implant data is illustrated using implant 100 as an example. The implant sensors 105*a*-105*e* and/or transponder 135 may be in communication with an external reader 600 (e.g., an RF reader). Sensors 105*a*-105*e* and/or transponder 135 may transmit data to reader 600 at the desired frequencies. Optionally, reader 600 may transmit one or more signals to sensors 105*a*-105*e* and/or transponder 135, such as, for example, signals configured to induce sensors 105*a*-105*e* and/or transponder 135 to transmit data. Reader 600 in turn may communicate the data to a cloud-based server 300. Cloud-based server 300 may be accessible via one or more electronic devices 700*a*-700*c* (e.g., a laptop 700*a*, a smartphone 700*b*, and/or other mobile device such as a tablet 700*c*). For example, cloud-based server 300 may be in two-way communication with one or more devices 700*a*-700*c*. In some examples, reader 600 may communicate directly with one or more devices 700*a*-700*c*.

Data communicated from the implant 100 (e.g., from one or more sensors 105*a*-105*e* and/or transponder 135) to reader 600 may include, for example, measurements or detection of various parameters (e.g., temperature), a serial number or other identifying or reference number of the sensor, and/or a lot number or other manufacturing information of the implant 100 such as, e.g., manufacturer name, implant dimensions and/or shape, etc. When the data includes identifying numbers or other information for each sensor, such data may be used to determine the location of the respective sensors.

As mentioned above, the sensors 105a-105e and/or transponder 135 may include circuitry that assists in filtering noise from raw data, or otherwise improving the signal-to-noise ratio of the transmitted data. Data collected and/or filtered by the transponder may be transmitted, communicated, or otherwise conveyed to the external reader 600 (e.g., RF reader). The reader 600 may include a graphic display (e.g., an LED display). In some examples, the reader 600 may include and/or be in communication with firmware or software that includes instructions for analyzing data, filtering data, collating data, sorting data, organizing data, presenting data on a display, and/or providing a notification signal. For example, one or more sensors 105a-105e and/or transponder 135 may communicate raw data to the reader 600, which may be analyzed via an algorithm, optionally via a remote server, that assists in filtering noise from raw data, or otherwise improving the signal-to-noise ratio of the implant data. In some embodiments, reader 600 may communicate a notification or event to a user. For example, a notification signal may be a recommendation displayed on the reader 600 that the patient contact his/her caregiver or clinician to follow up on a particular action item.

Reader 600 may be included in a handheld device or microdevice suitable for keeping on the patient's body in relatively close proximity to the implant 100. Reader 600 optionally may be handheld and/or incorporated into an article of clothing or accessory to be carrier by the patient throughout the day. For example, the reader 600 may be integrated into a bracelet, necklace, brooch, brassiere, blouse, scarf, vest, or other article that can be worn or carried. The reader 600 may be integrated into a handheld device that can be held by a user (e.g., patient or healthcare professional) in proximity to the implant 100, to receive data from the implant 100. The reader 600 may be used to read data from the implant 100 (e.g., implant data including one or more temperature measurements) continuously (e.g., while the reader 600 is integrated into an article of clothing), semi-continuously (e.g., at regular intervals, such as once per hour, once every 15 minutes, etc.), and/or on-demand at periodic intervals (e.g., when activated by the patient or other user).

Thus, sensors 105a-105e of implant 100 may be activated when reader 600 is in close proximity. Therefore, sensors 105a-105e can be configured to transmit data (e.g., temperature data) when in proximity to a corresponding reader 600 and/or after receiving a signal from the reader 600. Additionally or alternatively, sensors 105a-105e may be configured to continuously transmit data upon detection of a reader 600 within communication range. Additional methods of transmitting data disclosed in WO 2017/137853, incorporated by reference herein, may be used.

After the reader 600 receives data (e.g., implant data including one or more temperature measurements) from the implant 100 (e.g., tissue expander), the reader 600 may transmit the implant data to a device 700 (e.g., smartphone 700b, tablet 700c, laptop 700a, etc.). For example, the reader 600 may transmit, via 4G, 5G, other wireless network, or a wired connection, implant data to a cloud-based server 300 or other remote memory. The implant data on the cloud-based server 300 or remote memory may then be accessed by the device 700 (e.g., smartphone 700b, tablet 700c, laptop 700a, etc.).

One or more devices 700 may include software (e.g., an application including algorithms) that allows a user to interface with implant data stored on the cloud-based server or remote memory. In some embodiments, the device 700 can access a web-based application that allows the user to interface with implant data. A healthcare professional, or other user, may be able to track implant data via the device 700. Software accessed by the device may assist the user in tracking the implant data (e.g., temperature data) measured at each reading, may identify trends, create reports, and/or generate alerts when a significant change is detected. The software may include pattern recognition algorithms to identify changes, trends, patterns, cycles, and clinical indicators. For example, after surgery (e.g., implantation of the implant 100), the temperature of tissue around the implant 100 may be monitored constantly or periodically. Consistent increases in average temperatures may indicate an infection or adverse reaction to the implant 100. Patterns detected within the monitored temperature data may also indicate a reproductive condition of the patient, such as, for example, a pregnancy, ovulation, or hormonal activity affecting the reproductive system. The software accessed by devices 700 may help a healthcare professional manage the care of several patients, for example, through the development of a profile for each patient (e.g., a patient profile).

Various aspects of applications, software, or other programs or instructions executable by the device 700, in relation to implant data, are described with reference to FIGS. 5A-5C and 6A-6C. It should be understood that aspects described in relation to one or more of the figures does not limit that aspect to the embodiments shown in the discussed figures. Rather the all of figures should be view in context of the entire specification, and as describing various aspects that may optionally be with the devices and systems described herein. The components and aspects of the interfaces described herein may be used in any arrangement or combination that allows for one or more users to interface with implant data stored on a cloud-based server 300 or other remote memory.

Some of the aspects described herein may be restricted to a type or class of user profile. For example, the software described herein may allow for the creation of user profiles. User profiles may include profiles for patients as well as profiles for physicians or other healthcare professionals. Depending on the profile, and/or the type of profile, different aspects of the software described herein may be available or accessible. For example, a patient profile may also the user (e.g., a patient) to view data related to their own implant (e.g., properties of the implant such as serial number, size, shape, etc.). A healthcare professional profile, may allow the user (e.g., a physician) to access data related to the implants of several patients. In some embodiments, the healthcare professional profile may have access to implant data including measurements (e.g., temperatures) recorded by the sensors 105. The healthcare professional profile may have more permissions to access, view, sort, track, classify, edit, or modify data, such as, for example, implant data stored on the cloud-based server 300, as compared to a patient profile.

Figure 5C:
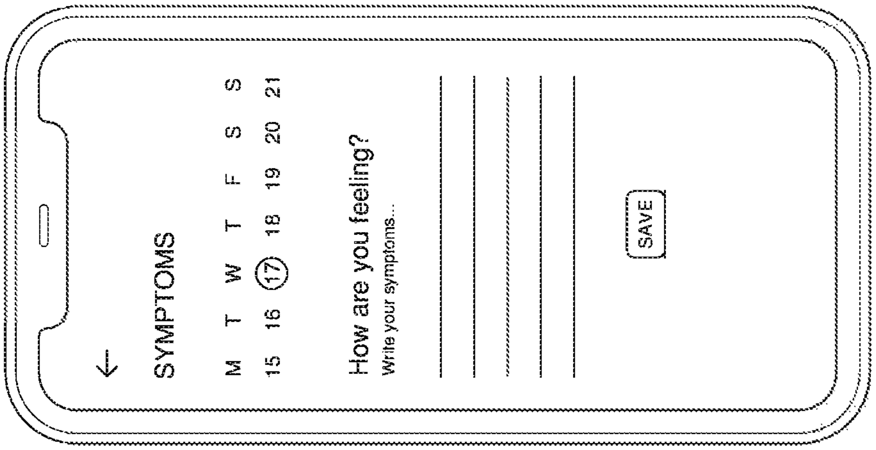
FIGS. 5A-5C and 6A-6C are schematics of aspects of a user interface for exemplary devices of the present disclosure.
Figure 5B:
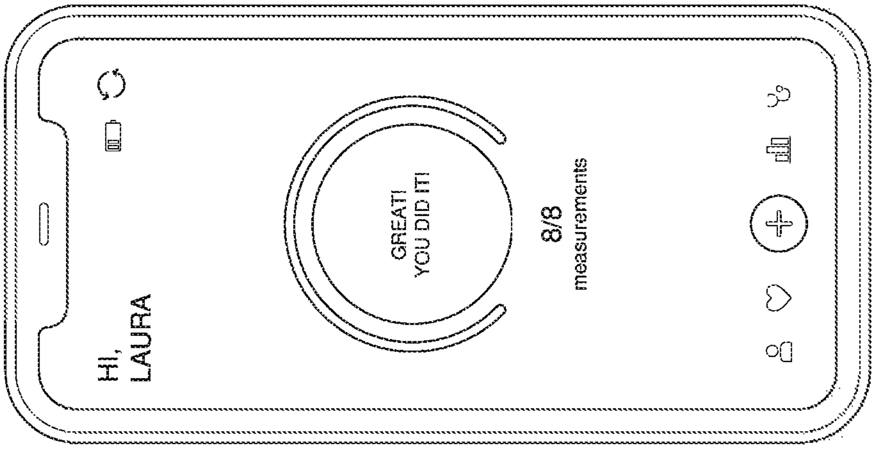
Figure 5A:
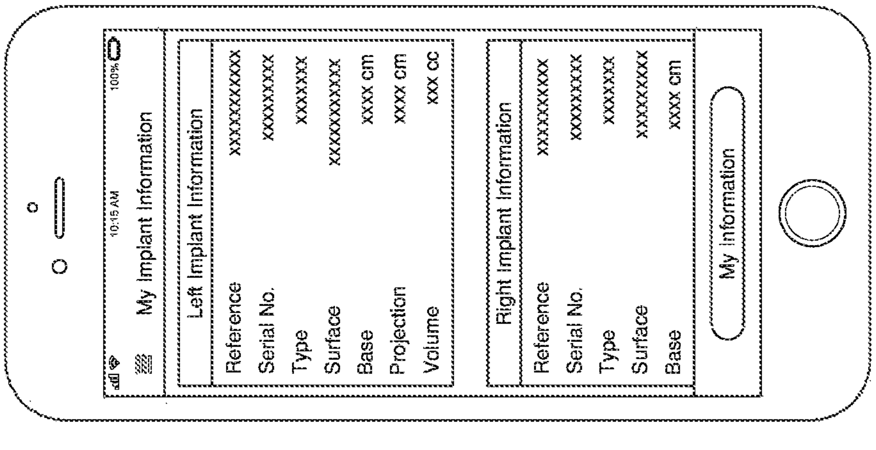

Referring to FIG. 5A, implant data may include data relating to the structure, size, condition, or other properties of implant 100 and/or sensors 105 within implant. For example, each implant 100 and each sensor 105 within each implant 100 may have one or more unique identifiers or codes. A status screen may allow a user (e.g., patient or healthcare professional) to view data related to one or more implanted implants 100 or sensors 105 of implants 100. The status screen may show one or more properties or conditions of the implanted devices such as, for example, a reference number, a serial number, a type of imprint, a shape, a size, a base size, a projection size, a volume, one or more other dimensions of the implant 100, a model type, an identifier, and/or whether signal is being received from one or more sensors 105 or transponders 135. The status screen may also provide a user with information regarding a physician or patient. For example, information about the patient (e.g., name, sex, age, weight, date of surgery, etc.) may be accessible in a healthcare professional profile, and information about the responsible physician (e.g., the implanting surgeon, oncologist, or other healthcare provider), such as their name or their contact information, may be accessible in a patient profile.

Referring to FIG. 5B, in some embodiments, device 700, or software of device 700 may assist a user (e.g., healthcare professional or patient) in obtaining measurements from implants 100. For example, the software may provide a step-by-step instruction process for a patient to use a reader 600 to obtain measurements from each sensor 105 of each implanted implant 100. The software and/or device 700 may prompt the user for each measurement, show pictorial graphics indicating where reader 600 should be placed to obtain measurements, display text or graphics representing the progress of the patient in obtaining prescribed measurements, and/or display implant data received by reader 600. The software may also allow a user to navigate between measurements to, for example, skip or repeat prescribed measurements.

Referring to FIG. 5C, device 700 may allow a user (e.g., a patient) to track or record their symptoms and/or condition. For example, the software may allow a user to record one or more metrics related to their condition or wellbeing and associate those recorded metrics with a date and/or time. The software may recognize, track, determine, or highlight any patterns in the provided metrics and conditions. The software may allow a healthcare professional profile associated with the patient's profile to access, view, and/or edit the patient's input symptoms and conditions.

Figure 6A:
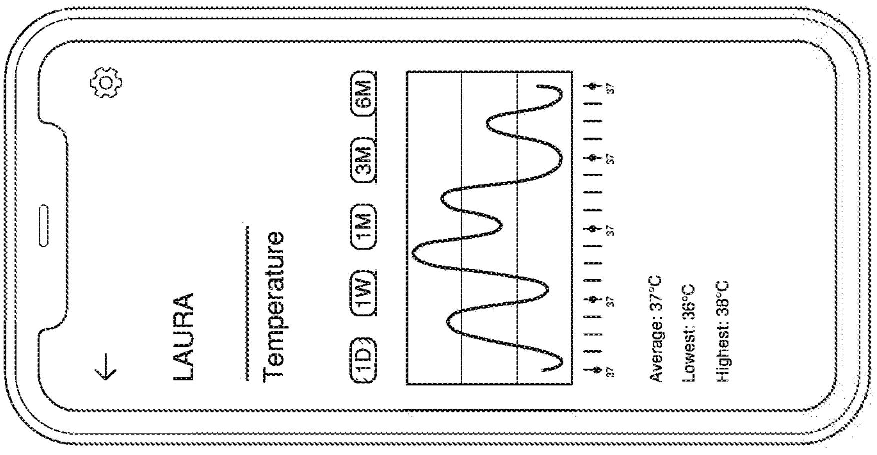

Referring to FIG. 6A, device 700 may allow a user to track, record, view, inspect, and/or analyze implant data collected over time. For example, device 700 may plot or otherwise graphically represent series of data, such as, for example, measurements (e.g., temperature measurements) collected by sensor(s) 105*a*-105*e* over time. The software may provide a statistical analysis of the collected data and/or may highlight or flag data points outside of threshold, boundary, or expected conditions. In some examples, the measurements may be grouped by time recorded and/or by location of sensor(s) 105*a*-105*e* providing the measurements. In this manner, a user (e.g., healthcare professional) may monitor trends in implant data from different regions or portions of the implant 100 (e.g., monitor temperature changes of tissue proximate one portion of implant 100 as compared to tissue proximate another portion of implant 100). In some embodiments, the measurements recorded and transmitted by sensors 105 (e.g., temperature measurements) may be accessible only to a healthcare professional profile.

Figure 6B:
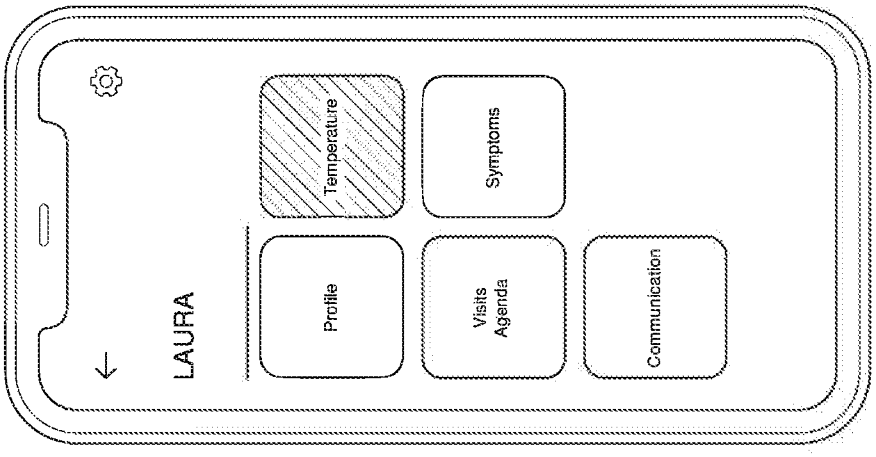

Referring to FIG. 6B, the software may allow a user to navigate between different aspects of the device interface. For example, a menu screen may allow a user to access one or more patient profiles, access one or more types of data (e.g., data about the implants 100 or data recorded by sensors 105), track physician/patient appointments, record and review symptoms and conditions, or contact another user. For example, the software may allow a patient user to contact their physician to schedule an appointment or may allow a healthcare professional user to review collected data and prompt a patient to collect more measurements, if necessary.

Figure 6C:
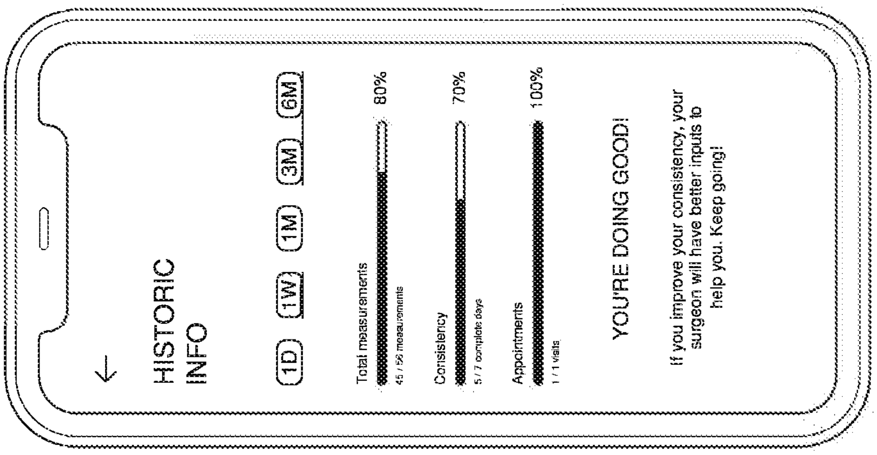

Referring to FIG. 6C, one or more profiles associated with a patient (e.g., a patient profile or a profile of a healthcare professional taking care of the patient) may access historical data regarding collection of measurements. This portion of the device interface may encourage, aide, or otherwise assist a user with collecting data from the sensors 105*a*-105*e*. Device may also prompt user to take more measurements upon detection that measurements have not be recorded for a pre-determined period of time.

Figure 7:
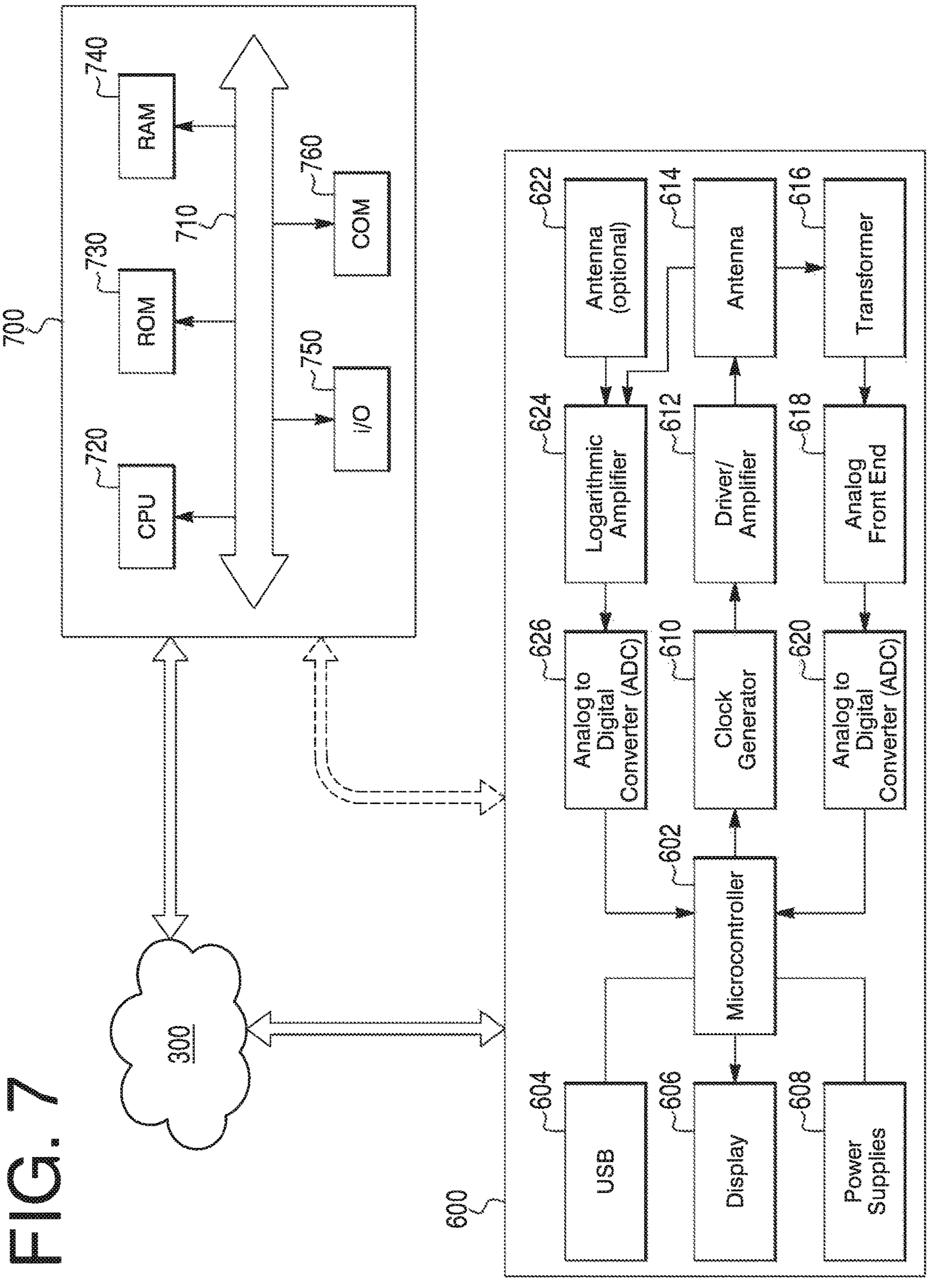
FIG. 7 is a block diagram describing one or more components of the system shown in FIG. 4.

FIG. 7 shows a block diagram of components of a reader 600 and device 700, both of which are in two-way communication with cloud-based server 300. Therefore, through cloud-based server 300, reader 600 and device 700 may communicate with each other. Additionally or alternatively, reader 600 and device 700 may communicate directly (e.g., with or without transferring data to and from cloud-based server 300). For example, reader 600 may communicate with device 700 via RF communication, a wired connection (e.g., USB cable), or over a local network. Similarly, device 700 may communicate with reader 600 via RF communication, a wired connection (e.g., USB cable), or over a local or global network.

Still referring to FIG. 7, reader 600 may include one or more of: a microcontroller 602, USB connections 604, displays 606, power supplies 608, clock generator 610, driver/amplifier 612, antenna 614, transformer 616, analog front end 618, one or more analog to digital converters (ADC) 620, 626, pickup antenna 622, or logarithmic amplifier 624.

Microcontroller 602 may be coupled to one or more USB connections 604 and displays 606. Reader 600 also may include one or more power supplies 608 connected to microcontroller 602. Microcontroller 602 may control clock generator 610, which may in turn control a driver/amplifier 612. Driver/amplifier 612 may be connected to an antenna 614. Antenna 614 may be connected to transformer 616, which may in turn be connected to an analog front end 618. An analog to digital converter (ADC) 620 may be connected to analog front end 618 and microcontroller 602. Antenna 614 and/or pickup antenna 622 may be connected to a logarithmic amplifier 624.

Microcontroller 602 may be, for example, a small computer on an integrated circuit, capable of receiving data from a variety of components, and also capable of directing a variety of components to perform their functions. For example, microcontroller 602 may contain one or more computer processing units (CPUs), as well as memory and programmable input/output peripherals. Microcontroller 602 may, for example, receive input and instructions via a digital connection, which may, for example, be a USB connection 604. In alternate embodiments, USB connection 604 may be another type of connection, such as an eSATA connection, a Firewire connection, an Ethernet connection, or a wireless connection. Connection 604 may connect microcontroller 602 to, for example, an input/output device capable of programming microcontroller 602, such as a computer.

Microcontroller 602 may also have a display 606, which may be, for example, an LED display. Display 606 may be configured to display calculations, input, output, and instructions sent and received by microcontroller 602. In some embodiments, display 806 may be configured to display instructions or input received via, e.g., connection 604. In alternate embodiments, display 606 may simply be a series of display lights. In further alternate embodiments, display 606 may be a non-LED display, such as an LCD display or other display.

Power supplies 608 may include any type of power supply compatible with elements of platform reader 600, including, for example, alternating current power supplies, direct current power supplies, battery power supplies, etc. In FIG. 8, power supplies 608 are shown as being connected to microcontroller 602. However, in further embodiments, power supplies may additionally or alternatively be one or more other components of reader 600.

Microcontroller 602 may be connected to clock generator 610, which may in turn be connected to driver/amplifier 612. Clock generator 610 may be a circuit that may provide a timed signal having a precise frequency and/or wavelength, through which microcontroller 602 may instruct driver/amplifier 612 to output a sweep of broadcast signals at a desired speed or interval. Driver/amplifier 612 may include, for example, a driver that generates an RF signal, and an electronic amplifier that may generate a low-power RF signal and amplify the signal into a higher power signal. Driver/amplifier 612 may include, for example, any type of RF driver/amplifier known in the art, such as either a solid state or a vacuum tube amplifier.

Driver/amplifier 612 may be connected to antenna 614. Antenna 614 may be, for example, an RF antenna. Antenna 614 may, on the one hand, be connected to transformer 616, which is in turn connected to analog front end 618 and ADC 620. Together, transformer 616, analog front end 618, and ADC 620 may be configured to receive and process signals, e.g., carrier and modulated signals, from antenna 614 and convert them to digital values, for return to microcontroller 602. In particular, transformer 616 may be configured to transform a received high voltage signal from antenna 618 and transform it to a voltage that may be processed by other elements of reader 600 (e.g., analog front end 818, ADC 820, and/or microcontroller 602) without damaging those other elements. Analog front end 618 may be configured to filter out portions of received and transformed signals from transformer 616. For example, analog front end 618 may be configured to process received signals such that carrier signals having the same wavelength and/or frequency as signals broadcasted by antenna 614 are removed, leaving only modulated signals (e.g., signals modulated by a transponder which received and returned a signal from antenna 614). ADC 620 may be configured to convert the filtered modulated signal to a digital value.

Pickup antenna 622 may serve as an additional antenna configured to assist in picking up weaker signals. Weak signals received by either antenna 614 or pickup antenna 622 may be amplified by logarithmic amplifier 624 and passed to ADC 26. Logarithmic amplifier 8624 may be an amplifier configured to receive weak signals and amplify them on a logarithmic scale, such that they may be processed by ADC 626 and microcontroller 602. ADC 626 may be configured to convert signals received from logarithmic amplifier 624, and provide them to microcontroller 602, which may be configured to assess the strength of signals received from ADC 626. In this manner, reader 600 may be able to evaluate and process signals spanning a breadth of signal strength.

In some embodiments, microcontroller 602 may be, for example, connected directly to driver/amplifier 612. In such embodiments, microcontroller 602 may be configured to provide a signal frequency and wavelength directly to driver/amplifier 602, without generation of the signal by clock generator 610.

Elements of reader 600 may be permanently or removably connected to one another. For example, components of reader 600 may be rearranged, such that units, components, or modules of the system may connect to alternative or additional units, components, or modules, other than those shown in FIG. 8.

A reader 600 (e.g., an RF reader) as discussed above may communicate implant data to a device (e.g., smartphone, tablet, laptop, desktop computer, etc.), either directly, or via a remote database (e.g., cloud-based storage 300). As shown in FIG. 7, such devices 700 may include a central processing unit (CPU) 720. CPU 720 may be any type of processor device including, for example, any type of special purpose or a general-purpose microprocessor device. CPU 720 also may be a single processor in a multi-core/multiprocessor system, such system operating alone, or in a cluster of computing devices operating in a cluster or server farm. CPU 720 may be connected to a data communication infrastructure 710, for example, a bus, message queue, network, or multi-core message-passing scheme.

Device 700 also may include a main memory 740, for example, random access memory (RAM), and also may include a secondary memory 730. Secondary memory 730, e.g., a read-only memory (ROM), may be, for example, a hard disk drive or a removable storage drive. Such a removable storage drive may comprise, for example, a magnetic tape drive, an optical disk drive, a flash memory, or the like. The removable storage drive in this example reads from and/or writes to a removable storage unit in a well-known manner. The removable storage unit may comprise a magnetic tape, optical disk, or other memory component which is read by and written to by the removable storage drive. Removable storage units generally include a computer usable storage medium having stored therein computer software and/or data.

In alternative implementations, secondary memory 730 may include other similar means for allowing computer programs or other instructions to be loaded into device 700. Examples of such means may include a program cartridge and cartridge, a removable memory chip (such as an EPROM, or PROM) and associated socket, and other removable storage units and interfaces, which allow software and data to be transferred from a removable storage unit to device 700.

Device 700 also may include a communications interface ("COM") 760. Communications interface 760 allows software and data to be transferred between device 700 and external devices, such as, for example, the reader or cloud-based storage system. Communications interface 760 may include a modem, a network interface (such as an Ethernet card), a communications port, a PCMCIA slot and card, or the like. Software and data transferred via communications interface 760 may be in the form of signals, which may be electronic, electromagnetic, optical, or other signals capable of being received by communications interface 760. These signals may be provided to communications interface 760 via a communications path of device 700, which may be implemented using, for example, wire or cable, fiber optics, a phone line, a cellular phone link, an RF link, or other communications channels.

Device 700 also may include input and output ports 750 to connect with input and output devices such as keyboards, mice, touchscreens, monitors, displays, etc. In some embodiments, the cloud-based server 300 may be structural similar to device 700. For example, cloud-based server 300 may include a bus 710, a CPU 720, a secondary memory 730, a main memory 740, input and output ports 750, and/or a communications interface 760. Cloud-based server 300 may perform any of the functions of device 700 described herein.

The principles and representative examples of the present disclosure have been described in the foregoing description and accompanying figures. However, aspects of the present disclosure are not to be construed as limited to the particular examples and embodiments disclosed. Further, the examples described herein are to be regarded as illustrative rather than restrictive. It will be appreciated that variations and changes may be made, and equivalents employed, without departing from the spirit of the present disclosure. Accordingly, it is expressly intended that all such variations, changes, and equivalents fall within the spirit and scope of the present disclosure, as claimed.

The invention claimed is:

1. A medical implant comprising:
a flexible shell;
a plurality of sensors; and
a base molded with indentations corresponding to the plurality of sensors such that the base has an approximately uniform thickness and is substantially flat when sensors are incorporated into the base, the plurality of sensors disposed in the indentations, the base sealed to the flexible shell such that the plurality of sensors are encompassed between the flexible shell and an interior surface of the base, the plurality of sensors being distributed at different locations of the base;
wherein each sensor of the plurality of sensors comprises an electromagnetic coil and an application-specific integrated circuit (ASIC);
wherein each sensor of the plurality of sensors is configured to measure a parameter including at least one of temperature or pressure;
wherein each sensor of the plurality of sensors is configured to transmit data related to the parameter:
at a frequency different from a frequency of one or more of other sensors of the plurality of sensors; and
at a time different from a time of the one or more of the other sensors of the plurality of sensors; and
wherein each sensor of the plurality of sensors includes a device identifier different from device identifiers of the one or more of the other sensors of the plurality of sensors.

2. The medical implant of claim 1, wherein, for each sensor of the plurality of sensors, the ASIC is coupled to the electromagnetic coil and disposed at or proximate a center of the electromagnetic coil, the ASIC being configured to measure the parameter.

3. The medical implant of claim 1, wherein the medical implant is a tissue expander that includes a port configured to receive and evacuate a fluid.

4. The medical implant of claim 3, wherein the port includes a transponder in communication with each sensor of the plurality of sensors.

5. The medical implant of claim 1, wherein each sensor of the plurality of sensors transmits the data related to the parameter at a frequency between about 100 kHz and about 250 kHz.

6. The medical implant of claim 1, wherein the plurality of sensors includes:
a first sensor in a superior portion of the base;
a second sensor in a first lateral portion of the base;
a third sensor in a second lateral portion of the base, where the first lateral portion is on an opposite side of a vertical plane bisecting the medical implant, from the second lateral portion; and
a fourth sensor in an inferior portion of the base.

7. The medical implant of claim 1, wherein the base has a thickness greater than a thickness of the flexible shell.

8. The medical implant of claim 1, wherein the medical implant does not include ferromagnetic materials.

9. The medical implant of claim 1, wherein each sensor of the plurality of sensors:
has a cylindrical, oval, circular or rectangular shape; and
includes an enclosure around the electromagnetic coil, the enclosure comprising glass or a ceramic.

10. The medical implant of claim 1, wherein the medical implant further includes:
one or more radiopaque markers, wherein the one or more radiopaque markers are coupled to or integrated into an anterior side of the flexible shell opposite the base; and
one or more tabs coupled to the flexible shell or the base for securing the medical implant to tissue.

11. The medical implant of claim 1 wherein the medical implant is a breast implant, gluteal implant, or tissue expander.

12. The medical implant of claim 1, wherein the plurality of sensors includes at least one sensor at or proximate a center of the base and two or more other sensors approximately equidistant from the center of the base.

13. The medical implant of claim 11, wherein the medical implant is a tissue expander comprising a port, the port including a transponder in communication with the plurality of sensors.

14. A system comprising:
a medical implant comprising:
a flexible shell;
a plurality of sensors; and
a base molded with indentations corresponding to the plurality of sensors such that the base has an approximately uniform thickness and is substantially flat when sensors are incorporated into the base, the plurality of sensors disposed in the indentations, the base sealed to the flexible shell such that the plurality of sensors are encompassed between the flexible shell and an interior surface of the base, the plurality of sensors being distributed at different locations of the base;
wherein the plurality of sensors includes:
at least three sensors in different indentations of the base spaced apart; and
each sensor of the plurality of sensors comprising an electromagnetic coil and an application specific integrated circuit (ASIC);
wherein each sensor of the plurality of sensors is configured to measure data, the data including at least one of temperature or pressure;
a reader configured to communicate with each sensor of the plurality of sensors; and
a computer configured to receive communications from the reader.

15. The system of claim 14, wherein each sensor of the plurality of sensors is configured to transmit the data to the reader:
at a frequency different than a frequency of other sensors of the plurality of sensors;
at a time different from a time of the other sensors of the plurality of sensors; and
with a device identifier different from another device identifier associated with other sensors of the plurality of sensors.

16. A method of obtaining information for a patient with an implant, the implant comprising a flexible shell, a plurality of sensors, and a base, the method comprising:
transmitting data from the plurality of sensors to an external reader; and communicating the data to a cloud-based server;

wherein each sensor of the plurality of sensors:

transmits the data at a frequency different from a frequency of one or more of other sensors of the plurality of sensors;

transmits the data at a time different from a time of the one or more of the other sensors of the plurality of sensors; and includes a device identifier different from device identifiers of the one or more of the other sensors of the plurality of sensors;

wherein the base is molded with indentations corresponding to the plurality of sensors such that the base has an approximately uniform thickness and is substantially flat when sensors are incorporated into the base, the plurality of sensors disposed in the indentations, the base sealed to the flexible shell such that the plurality of sensors are encompassed between the flexible shell and an interior surface of the base, the plurality of sensors being distributed at different locations of the base.

17. The method of claim 16, wherein the data transmitted by the plurality of sensors includes a temperature of an area of patient tissue proximate each sensor of the plurality of sensors.

18. The method of claim 16, wherein the data is transmitted at least periodically.

19. The method of claim 16, wherein the external reader is a handheld device or incorporated into an article of clothing or an accessory.

20. The method of claim 16, wherein the data provides information about a status of patient tissue surrounding the implant and information about a health condition of the patient.

* * * * *